United States Patent [19]

Milewski et al.

[11] Patent Number: 4,755,174

[45] Date of Patent: Jul. 5, 1988

[54] APPARATUS FOR ADMINISTERING FLUIDS THROUGH THE NOSE BY MEANS OF A TUBE

[76] Inventors: Christian Milewski, D-6500 Mainz-Gonsenheim, 14-Nothelferstr. 26, Fed. Rep. of Germany; Peter Welzer, D-6500 Mainz-Finthen, Sartoriusring 27, Fed. Rep. of Germany

[21] Appl. No.: 863,964

[22] Filed: May 16, 1986

[30] Foreign Application Priority Data

May 17, 1985 [DE] Fed. Rep. of Germany ....... 3517747

[51] Int. Cl.⁴ ........................ A61M 15/08; A62B 7/00
[52] U.S. Cl. ................................ 604/174; 128/207.18
[58] Field of Search ................. 128/207.18, 342; 604/94, 104, 174, 179, 256, 280, 283

[56] References Cited

U.S. PATENT DOCUMENTS

| | | | |
|---|---|---|---|
| 2,179,964 | 11/1939 | Stevens | 128/342 |
| 3,161,199 | 12/1964 | Sands | 604/179 |
| 3,260,258 | 7/1966 | Berman | 128/342 |
| 3,568,678 | 3/1971 | Pourquier et al. | 604/174 |
| 4,193,174 | 3/1980 | Stephens | 128/207.18 |
| 4,280,493 | 7/1981 | Council | 128/342 |
| 4,634,425 | 1/1987 | Meer | 604/174 |

Primary Examiner—Stephen C. Pellegrino
Assistant Examiner—Ralph Lewis
Attorney, Agent, or Firm—Omri M. Behr

[57] ABSTRACT

An apparatus for administering fluids through the nose by means of a tube is provided which comprises a tube having a distal end and a proximal end. The proximal end of the tube when no administration is being carried out is secured in position and disposed removably within the nasal vestibule for the administering. This ensures that during this time when no administering is being carried out, the proximal end of the tube is mounted invisibly within the nose whilst for administering the fluid it can easily be removed from the nasal vestibule and connected to the fluid container.

7 Claims, 1 Drawing Sheet

APPARATUS FOR ADMINISTERING FLUIDS THROUGH THE NOSE BY MEANS OF A TUBE

BACKGROUND OF THE INVENTION

The invention relates to an apparatus for administering fluids through the nose by means of a tube having a distal end and a proximal end.

Such apparatus are known, for example, in the field of artifical feeding. For thus purpose, a tube is usually introduced through the nose of the patient who frequently depends on arificial feeding for a very long time, in such a manner that the distal end of the tube is located in the stomach area, while the proximal end of the tube is disposed outside the nose and is accessible from the outside. In known apparatuses, the proximal end is secured on the nose or adjacent parts of the face by means of adhesive plaster to prevent it from slipping either back in or out during those times when no feeding is taking place.

A disadvantage of the known apparatuses is that the proximal end of the tube is visible because of the manner in which it is secured. In particular for patients who require long artificial feeding because of their illness, this visibility has the disadvantage that their dependence on this type of nutrition and thus the existence of their illness is obvious to everyone. With many patients, this in turn, leads to negative phychic effects. In addition, the visible securing of the proximal end of the nose tube represents a substantial impairment of the outer appearance of the patient.

The catalog of the company, Rusch Chirurgie, #III/3, 2nd. Ed., 1977, page 14 and page 36, shows a feeding tube or pneumatic nose tube. The feeding tube shown here has the aforementioned known problems, i.e., it is led out of the nose of the patient and thus represents a visible impairment of the patient.

The pneumatic nose tube consists of a body which fills the nasal cavity and from which a connection piece extends both into the nostril and projects out of the nostril so that it also represent a visible impairment of the patient.

In order to solve the aforementioned problems in using feed tubes, the operative insertion of the tube into the immediate region of the stomach has been suggested, but this was unacceptable in practice. Many patients do not want the necessary surgical intervention and with some the intervention is either not possible or leads to additional undesired risks.

The problem to be solved by the invention is therefore, the provision of a device for administering fluids through the nose by means of a tube of the type outlined above, which makes it possible to avoid impairing the patient by visible fixing of the proximal end of the tube.

SUMMARY OF THE INVENTION

This problem is solved by the provision of a device in which the proximal end 4 of the tube is mounted in a bearing member whose outer form is adapted to the contour of the nasal vestibule. The tube needs to be removed from the nose only in order to be connected with the fluid container or a tube extension piece, for administering the fluid, for example in artificial feeding. During the time when there is no administration, the proximal end is disposed within the nose vestibule and is thus invisible so that the dependency of the patient who requires lengthy, continuous administration, for example, permanent artificial feeding, is no longer obvious.

In addition, the proximal end of the tube is secured in position in the time when no administration is taking place, so that there is no danger of it slipping through the nose rearwardly into the body or slipping completely out of the nose leaving the patient, nevertheless, every freedom of movement.

In supporting the proximal end of the tube at the inner nasal flap, natural conditions are advantageously utilized to prevent a rearward slipping down of the tube.

The end of the tube may be provided with a connector which has a support face. In a further advantageous embodiment, the connector may be constructed as conventional commercially tube connector, which represents a particularly economical solution.

As a further advantageous development, the connector can be disposed in a bearing member introduceable into the nasal vestibule, thereby making the use of the apparatus according to the invention more pleasant and easier for the patient.

The bearing member can, in turn, bear on the nasal flap while the support face of the connector can bear on a bearing face of the bearing member, providing a further improvement in the useful properties of the apparatus of the present invention.

Since the bearing face of the bearing member must have a hard surface to ensure a permanently secure fit against the slipping out of the tube, when this bearing face is disposed in a cavity of the bearing member the nose inner wall cannot come into contact with the bearing face, this avoiding injuries and unplesantness to the patient.

In one embodiment the cavity is provided with recesses on two sides. Upon introduction into the nasal vestibule, one recess is pointed towards the nostril, and in the other towards the nasal flap. This achieves the advantage that natural anatomical orientations are taken fully into account so that the recesses are so sized that even when the bearing member and connector disposed therein are introduced into the nasal vestibule, enough free space is present to prevent obstruction of the patient during breathing.

In yet another embodiment the cavity of the bearing member has a subregion within which the entire connector can be secured without possibility of slippage during the time when no administration is being conducted. The advantage is that any danger of injury and unpleasantness for the patient is eliminated in the time in which the proximal end of the tube is disposed within the nasal vestibule.

The support properties of the bearing member may be optimized by finishing the surface thereof to reduce its roughness to a desirable level suitably, the bearing member consists of a physiologically compatible material.

To avoid the flowing back of the stomach content through the proximal end of the tube connector thereof may be made closable. Suitably, a removable closure stopper or plug can be used.

Further embodiments such as those wherein the bearing face is formed as thread and where the cavity is open only one side, suitably wherein a guide pin for the recess of the connector is disposed at the wall face are desirable, since the production of the apparatus according these embodiments can be carried out very simply and economically.

A further improvement in the support and wearing properties can be obtained if the outer contour of the bearing member is adapted to the inner contour of the nasal vestibule, it being possible to make a contour which is suitable for great number of differently shaped nasal vestibules. Of course, it is also possible to fit the bearing member individually.

BRIEF DESCRIPTION OF THE DRAWINGS

Further details, features and advantages of the invention will be apparent from the following description of examples of embodiment with the aid of the drawings, wherein.

DESCRIPTION OF THE PREFERRED EMBODIMENTS

The first embodiment, shown in FIGS. 1 to 5 illustrate an apparatus according the the invention for administration fluids through the nose comprises a bearing member 1, a tube 2 and in the case of the example, a connector or adapter 3. The tube is shown only in the region of its proximal end 4. The distal end of the tube 2, after introduction is located in an interior point of the body to which the particular fluid is to be supplied. In the case of artificial feeding, which is the example taken hereinafter, the distal end is disposed in the region of the patient's stomach.

Figure 1:
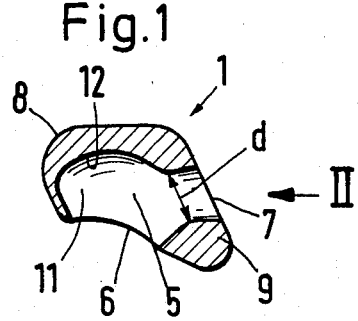
FIG. 1 is a cross-sectional view of a bearing member of a first embodiment of the apparatus according to the invention.

The bearing member 1 illustrated in FIG. 1 comprises, in the example shown, a cavity 5 which is open at two sides and recesses 6 and 7. The recess 6 corresponds to that which when the bearing member 1 is introduced into the nasal vestibule is located adjacent the nostril. The recess 7 accordingly points, in this condition, towards the nasal flap. This further means that the upper region 8 of the bearing member 1 on the left in the illustration of FIG. 1 when introduced into the nasal vestibule bears on the forwardly pointing upper inner region thereof whilst the subregion 9 of the bearing member lying at the bottom right is disposed in the rear lower region of the nasal vestibule.

Figure 2:
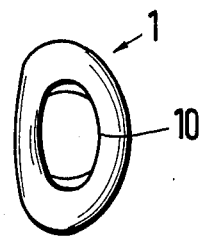
FIG. 2 is a view of the bearing member from the direction of the arrow II in FIG. 1.
Figure 3:
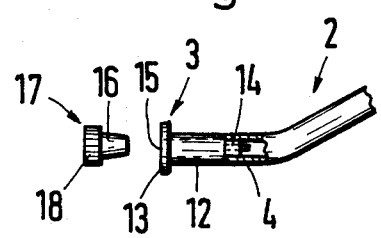
FIG. 3 shows the region of the proximal end of a tube of the apparatus according to the invention together with a connector.
Figure 4:
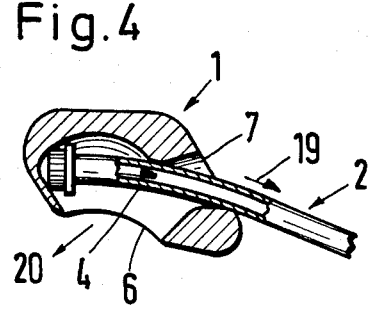
FIG. 4 is a view corresponding to FIG. 1 of the bearing member in which the proximal end of the tube with the connector is arranged according to FIG. 3. This illustration corresponds to the orientation of the arrangement when no administration is being carried out.
Figure 5:
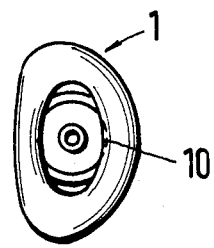
FIG. 5 is a view of the bearing member according to FIGS. 1 and 4 corresponding to FIG. 2 with connector supported therein according to FIG. 3, this arrangement being shown during administration.

The bearing member 1 further comprises a bearing face 10 illustrated in FIGS. 2 and 5 which is disposed within the cavity 5 in the region of the cross-section denoted by d in FIG. 1 and which according to FIGS. 2 to 5 has an ellipsoidal form. This form has the advantage that the bearing face 10 firstly provides secure support not only in the region of the minor ellipse diameter, but also in the region of the major ellipse diameter. Circular circumferences of the support face 13 engage the bearing face 10, leaving enough free space for unobstructed passage of respiratory air.

Furthermore, the recesses 6 and 7 also have dimensions large enough to permit passage of respiratory air. Also, the size of the recess 7 is chosen such that when inserted into the bearing member 1 the proximal end 4 of the tube 2 is allowed adequate freedom of movement to be able to follow the movements of the patient. The size of recess is size such that removal of the proximal end 4 through said recess 6 is possible even when the connector 3 is fitted.

The arrangement of the bearing face 10 within the cavity 5 ensures that the hard surface of the bearing face 10, necessary for ensuring a reliable retaining function, cannot cause any injuries or unpleasantness whatever to the patient.

The bearing member 1 is further adapted in its outer contour to the inner contour of the nasal vestibule, resulting in the olive-like form apparent in FIGS. 2 and 5, for which reason the bearing member 1 can also be referred to as a "nose olive".

The cavity 5 of the bearing member 1 further comprises a subregion 11 which is bordered by a rounded wall region 12 of the cavity 5. The function of this subregion 11 will be explained in detail hereinafter.

The connector 3 illustrated in FIG. 3 comprises a cylindrical body 12 which at one side is provided with a support face 13, which, in the illustrated example, is of circular cross-section. The opposite end of connector 3 comprises an insert pin 14 over which the proximal end 4 of the tube 2 can be pushed. The connector 3 is hollow on the inside so that a flow connection can be established between the connector 3 and the fitted tube 2. The embodiment of the connector 3 illustrated in FIG. 3 represents a conventional commercially available tube connector, whose flange-shaped support face 13 comprises a recess 15 into which a pin 16 of a closure stopper 27 can be introduced, thus enabling the open end of the connector 3 to be sealed. The closure stopper 17 comprises a knurled plug end 18 by means of which the stopper 17 can be introduced into or removed from the recess 15.

FIG. 4 shows the manner in which the connector 3 provided with the stopper 17 can be disposed in the bearing member 1 when the apparatus is not in use. That is to say during the time when no feeding is taking place and the bearing member 1 is located in the nasal vestibule. For this purpose the region of the support face 13 on which the stopper 17 is disposed is introduced into the subregion 11 of the cavity 5, the connector 3 with the stopper 17 and the support face 13 bearing on the inner wall face 12 of the subregion 11. The cylindrical body 12 and the connection pin 14 of the connector 3 are then in the lower region of the cavity 5 as illustrated in FIG. 4, the rounded form of the inner wall face 12 leaving the connector 3 enough freedom of movement to enable the proximal end of the tube 2 to move within the adequately large recess 7 so that is can follow the movements of the patient which produce movements of the tube 2.

When administration of fluid such as in artificial feeding is to be carried out, the bearing member 1 can be removed by finger pressure on the wing of the nose from the nasal vestibule, taking with it the proximal end 4 of the tube 2. The connector 3 can then be withdrawn from the subregion 11 of the cavity 5 by pulling the tube 2 in the direction of the arrow 19 and by pressing through the recess 6 in the direction of the arrow 20, pressed out of the bearing member 1. The stopper 17 can then be removed and the connector 3 connected to the corresponding counter piece of the fluid supply line. When the supply of the fluid is completed, the connector can be closed again and returned into the position with the bearing member 1, illustrated in FIG. 4. The bearing member 1 is again introduced into the nasal vestibule in which it is invisibly arranged with the proximal end 4 of the tube 2 is secured in position.

Securing tube 2 against undesirable slippage in the direction of the arrow 19 is ensured by engaging the support face 13 on the support face 10 of the bearing member 1 as illustrated in FIG. 5. It is apparent from this figure that the circular support face 13 in the regions shown in dashed line, bears on the bearing face 10 and consequently, a sliding back of the tube 2 into the interior of the body is prevented. However, tube 2 can move freely in the longitudinal direction of the recess 7 as is also apparent from FIG. 5 and already explained above.

Figure 6:
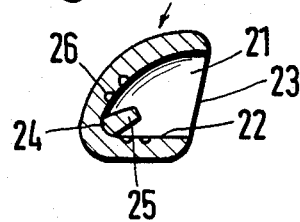
FIG. 6 shows a cross-sectional view of a bearing member of a second embodiment of the apparatus according to the invention corresponding to FIGS. 1 and 4.

Another embodiment of a bearing member 20 is illustrated in FIG. 6, which comprises a cavity 21 which is bordered by an inner wall face 22 of the bearing member 20. The bearing member 21 is open on one side via a recess 23 and comprises a guide pin 25 at the wall region 24 opposite the recess 23. In the region of said guide pin 25 in the inner wall face 22, a thread 26 is disposed which can cooperate with the support face 13 of the connector 3. Consequently, the connector 3 and the thus proximal end 4 of the tube 2 can be introduced into the bearing member 20 by rotating the connector 3 and secured therein by interaction of the support face 13 with the thread 26. The guide pin 25 supports the mounting of the connector 3. As regards its outer contour, surface structure and its function and arrangement in the nasal vestiuble, the bearing member 20 is otherwise constructed similarly to that of the embodiment of FIGS. 1 to 5 and consequently, the explanation with regard to these points also applies to the embodiment of FIG. 6. Furthermore, the connector 3 illustrated according to FIG. 3 can also be used together with the bearing member 20.

It should be added that the support face 13 can have, not only a continuous circular form, but rather also may comprise a plurality of radially projecting separate support elements, possibly serving as screw elements.

We claim:

1. Apparatus for administering fluids through the outer opening of a nostril by means of a tube having a distal end and a proximal end comprising
a bearing member having a passageway therethrough, said bearing member having an outer surface adapted to fit snugly into the nasal vestibule of the nostril in which it is utilized in such a manner that substantially no air can pass between said outer surface and said vestibule,
said passageway having an internal bearing face and connecting the outer opening of the nostril with the nasal cavity and having dimensions which are sufficient to permit the passage therethrough of a nasal feeding tube and which are greater at the end of the passageway proximal to the outer nostril opening than distal thereto,
a feeding tube having a distal end and a proximal end, and
a connector means adapted to fit into the proximal end of the feeding tube having a dimension perpendicular to the principle axis of the feeding tube greater than the minimum dimension of the said passageway but less then its maximum dimension and being adapted to rest against said internal bearing face.

2. An apparatus of claim 1 wherein said passageway has dimensions which are sufficient to permit the passage therethrough of a nasal feeding tube and a sufficient quantity of air to permit regular breathing.

3. An apparatus of claim 2 wherein said connector is provided with a flange.

4. An apparatus of claim 1 characterized in that the surface of the bearing member has a slight roughness and the bearing member consists of physiologically compatible material.

5. Apparatus for administering fluids through the outer opening of a nostril by means of a tube having a distal end and a proximal end comprising
a bearing member having a cavity therein,
said bearing member having an outer surface adapted to fit snugly into the nasal vestibule of the nostril whereby substantially no air can pass between said outer surface and said vestibule,
a feeding tube having a distal end and a proximal end,
a connector means adapted to fit into the proximal end of the feeding tube,
said cavity having a single opening facing the nasal cavity of sufficient size to admit said connecting means therein and an internal bearing face with means to releasably hold said connector means within said cavity.

6. An apparatus of claim 5 wherein said bearing face is provided with a thread, and said connector is provided with a plug means insertable therein, said plug means having an external thread interactable with the thread in said bearing face.

7. An apparatus of claim 5 wherein said bearing face is provided with a pin means insertable in said connector and the bearing face surrounding said pin means is provided with a thread interactable with the external surface of said connector.

* * * * *

UNITED STATES PATENT AND TRADEMARK OFFICE
CERTIFICATE OF CORRECTION

PATENT NO. : 4,755,174

DATED : July 5, 1988

INVENTOR(S) : Christian Milewski, Peter Welzer

It is certified that error appears in the above-identified patent and that said Letters Patent is hereby corrected as shown below:

IN THE DRAWINGS

Figure 3 should be deleted to appear as shown below:

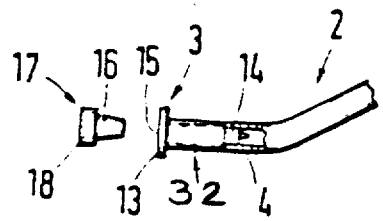

UNITED STATES PATENT AND TRADEMARK OFFICE
CERTIFICATE OF CORRECTION

PATENT NO. : 4,755,174

DATED : July 5, 1988

INVENTOR(S) : Christian Milewski, Peter Welzer

It is certified that error appears in the above-identified patent and that said Letters Patent is hereby corrected as shown below:

Column 1, Line 28, delete "phychic", insert --physic--.

Column 2, line 32, delete "unpleasantness", insert --unpleasantness--.

Column 4, line 29, delete "12", insert --32--.

line 40, delete "27", insert --17--.

Column 5, line 26, delete "21", insert --20--.

Signed and Sealed this

Twenty-fourth Day of January, 1989

*Attest:*

DONALD J. QUIGG

*Attesting Officer*      *Commissioner of Patents and Trademarks*